(12) United States Patent
Shin et al.

(10) Patent No.: US 8,044,080 B2
(45) Date of Patent: Oct. 25, 2011

(54) ISOXAZOLINE DERIVATIVE AND NOVEL PROCESS FOR ITS PREPARATION

(75) Inventors: Hyun Ik Shin, Daejeon (KR); Hyeong Wook Choi, Daejeon (KR); Tae Ho Heo, Daejeon (KR); Kyu Woong Lee, Daejeon (KR); Jae Hoon Lee, Daejeon (KR); Ki Sook Park, Daejeon (KR)

(73) Assignee: LG Life Sciences Ltd., Seoul (KR)

( * ) Notice: Subject to any disclaimer, the term of this patent is extended or adjusted under 35 U.S.C. 154(b) by 1099 days.

(21) Appl. No.: 11/816,801

(22) PCT Filed: Feb. 21, 2006

(86) PCT No.: PCT/KR2006/000576
§ 371 (c)(1),
(2), (4) Date: Aug. 21, 2007

(87) PCT Pub. No.: WO2006/090997
PCT Pub. Date: Aug. 31, 2006

(65) Prior Publication Data
US 2008/0262032 A1    Oct. 23, 2008

(30) Foreign Application Priority Data
Feb. 26, 2005   (KR) .................. 10-2005-0016203

(51) Int. Cl.
*A61K 31/42* (2006.01)
*C07D 413/12* (2006.01)
(52) U.S. Cl. ......... 514/378; 546/139; 548/240; 549/430
(58) Field of Classification Search ............ 514/378; 546/139; 548/240; 549/430
See application file for complete search history.

(56) References Cited

FOREIGN PATENT DOCUMENTS

| KR | 1999-79267 A | 11/1999 |
| WO | WO-01/21599 A1 | 3/2001 |
| WO | WO-01/21600 A1 | 3/2001 |
| WO | WO-2005/021516 A1 | 3/2005 |

OTHER PUBLICATIONS

Lewis Acid Coordinated Nitrile Oxide and Nitrile Imine 1,3-Dipoles. syn-Selective Cycloadditions to 2-(1-Hydroxyalkyl)acrylates, Bull. Chem. Soc. Jpn., vol. 66, pp. 2685-2693.
Synthesis of a Peptidyl Difluoro Ketone Bearing the Aspartic Acid Side Chain: An Inhibitor of Interleukin-1beta Convering Enzyme, J. Org. Chem., vol. 57, pp. 7309-7314.

*Primary Examiner* — Sabiha Qazi
(74) *Attorney, Agent, or Firm* — Birch, Stewart, Kolasch & Birch, LLP

(57) ABSTRACT

The present invention relates to an isoxazoline derivative having the cyclic carboxylic acid hemiketal moiety of formula (1) for use as caspase inhibitor, a process for preparing it, and a pharmaceutical composition comprising it.

19 Claims, 1 Drawing Sheet

[Fig. 1]
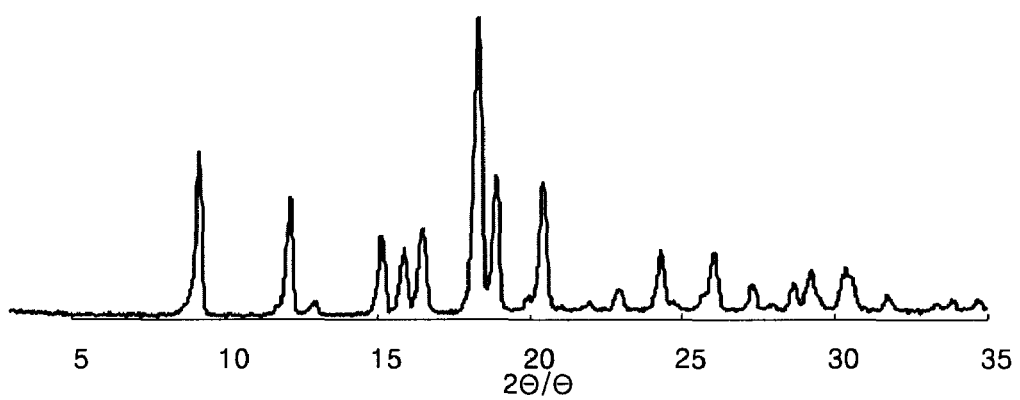
[Fig. 2]
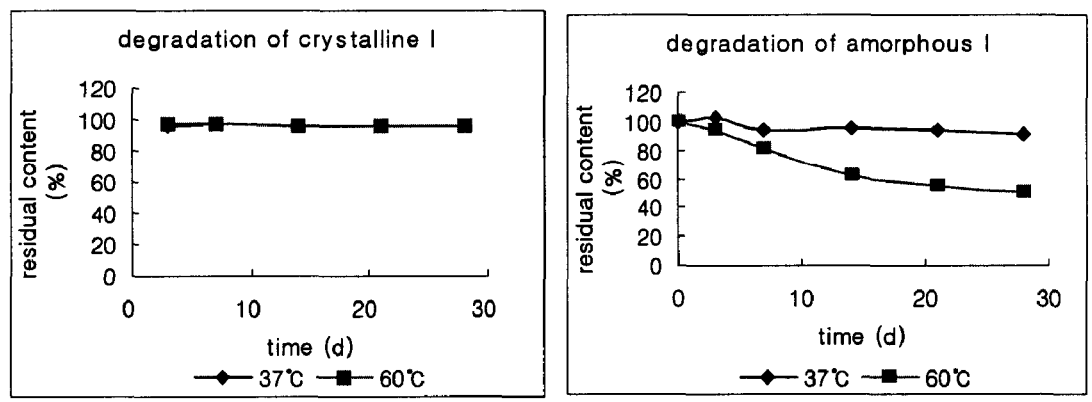

ISOXAZOLINE DERIVATIVE AND NOVEL PROCESS FOR ITS PREPARATION

TECHNICAL FIELD

The present invention relates to an isoxazoline derivative having cyclic carboxylic acid hemiketal moiety for use as a caspase inhibitor, a process for preparing it, a pharmaceutical composition comprising it, and a use thereof.

BACKGROUND ART

Caspase inhibitor refers to a compound that can inhibit caspase activity, thereby regulating inflammation or apoptosis caused by caspase function. Among caspase inhibitors, irreversible inhibitor is known to show more effective inhibition activity since it irreversibly inactivates an enzyme to control apoptosis (Wu J. et al., *Methods: A Companion to Methods in Enzymology* 1999, 17, 320). The following compounds are known as irreversible inhibitor, and have 3-amino-5-fluoro-4-oxopentanoic acid moiety in common.

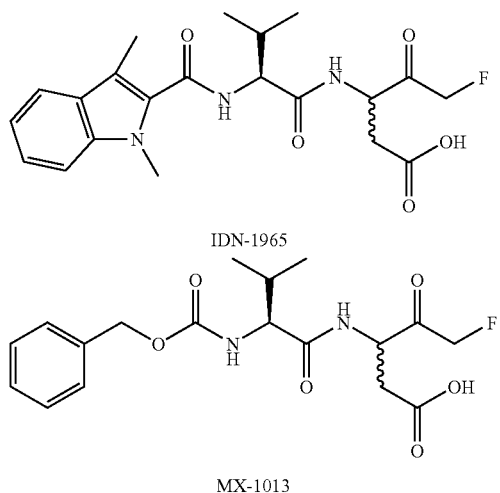

As diseases which can be treated or alleviated by administration of the above compounds, there are rheumatoid arthritis, inflammatory bowel disease, graft vs. host disease, sepsis, osteoarthritis, osteoporosis, acute and chronic myelogenous leukemia, meningitis, salpingitis, septic shock, cholangitis, colitis, encephalitis, endocarditis, glomerulonephritis, hepatitis, myocarditis, pancreatitis, Type I diabetes mellitus, multiple sclerosis, Alzheimer's disease, Parkinson's disease, hepatocirrhosis, etc.

REFERENCES

Dementia: Arch Neurol 2003 March; 60(3): 369-76, Caspase gene expression in the brain as a function of the clinical progression of Alzheimer disease. Pompl P N, Yemul S, Xiang Z, Ho L, Haroutunian V, Purohit D, Mohs R, Pasinetti G M.;

Cerebral stroke: Proc Natl Acad Sci USA 2002 Nov. 12; 99(23): 15188-93, Caspase activation and neuroprotection in caspase-3-deficient mice after in vivo cerebral ischemia and in vitro oxygen glucose deprivation. Le D A, Wu Y, Huang Z, Matsushita K, Plesnila N, Augustinack J C, Hyman B T, Yuan J, Kuida K, Flavell R A, Moskowitz M A.;

Brain impairment due to AIDS: J Neurosci 2002 May 15; 22(10): 4015-24, Caspase cascades in human immunodeficiency virus-associated neurodegeneration. Garden G A, Budd S L, Tsai E, Hanson L, Kaul M, D'Emilia D M, Friedlander R M, Yuan Masliah E, Lipton S A.;

Diabetes: Diabetes 2002 June; 51(6): 1938-48, Hyperglycemia-induced apoptosis in mouse myocardium: mitochondrial cytochrome C-mediated caspase-3 activation pathway. Cai L, Li W, Wang G, Guo L, Jiang Y, Kang Y J.;

Gastric ulcer: J Physiol Pharmacol 1998 December; 49(4): 489-500, Role of basic fibroblast growth factor in the suppression of apoptotic caspase-3 during chronic gastric ulcer healing. Slomiany B L, Piotrowski J, Slomiany A.;

Cerebral injury by hepatitis: J Viral Hepat 2003 March; 10(2): 81-6, Cerebral dysfunction in chronic hepatitis C infection. Forton D M, Taylor-Robinson S D, Thomas H C.;

Fulminant hepatic failure: Gastroenterology 2000 August; 119(2): 446-60, Tumor necrosis factor alpha in the pathogenesis of human and murine fulminant hepatic failure. Streetz K, Leifeld L, Grundmann D, Ramakers J, Eckert K, Spengler U, Brenner D, Maims M, Trautwein C.;

Sepsis: Nat Immunol 2000 December; 1(6): 496-501, Caspase inhibitors improve survival in sepsis: a critical role of the lymphocyte. Hotchkiss R S, Chang K C, Swanson P E, Tinsley K W, Hui J J, Klender P, Xanthoudakis S, Roy S, Black C, Grimm E, Aspiotis R, Han Y, Nicholson D W, Karl I E.;

Organ transplantation rejection: Xenotransplantation 2001 May; 8(2): 115-24, In vitro prevention of cell-mediated xeno-graft rejection via the Fas/FasL-pathway in CrmA-transducted porcine kidney cells. Fujino M, Li X K, Suda T, Hashimoto M, Okabe K, Yaginuma H, Mikoshiba K, Guo L, Okuyama T, Enosawa S, Amemiya H, Amano T, Suzuki S.;

Rheumatoid arthritis: Prog Med Chem 2002; 39: 1-72, Caspase inhibitors as anti-inflammatory and antiapoptotic agents. Graczyk P P.;

Ischemic cardiac diseases: Am J Physiol Heart Circ Physiol 2002 September; 283(3): H990-5, Hypoxia-induced cleavage of caspase-3 and DFF45/ICAD in human failed cardiomyocytes. Todor A, Sharov V G, Tanhehco E J, Silverman N, Bernabei A, Sabbah H N.;

Anti-inflammation: J Immunol 2003 Mar. 15; 170(6): 3386-91, A broad-spectrum caspase inhibitor attenuates allergic airway inflammation in murine asthma model. Iwata A, Nishio K, Winn R K, Chi E Y, Henderson W R Jr, Harlan J M.;

Hepatocirrhosis: i) J Pharmacol Exp Ther. 2004 March; 308 (3): 1191-6, The caspase inhibitor Idn-6556 attenuates hepatic injury and fibrosis in the bile duct ligated mouse. Canbay A., Fledstein A., Baskin-Bey E., Bronk F S. Gores G J.; ii) Hepatology. February; 39(2): 273-8, Apoptosis: the nexus of liver injury and fibrosis. Canbay A, Friedman S, Gores G J.; iii) Hepatology. 2003 November; 38(5): 1188-98, Kupffer cell engulfment of apoptotic bodies stimulates death ligand and cytokine expression. Canbay A, Feldstein A E, Higuchi H, Werneburg N, Grambihler A, Bronk S F, Gores G J.

On the other hand, for 3-amino-5-fluoro-4-oxopentanoic acid moiety of caspase inhibitor, such preparation process as the following Reaction Scheme 1 (Revesz et al., *Tetrahedron Lett.* 1994, 35, 9693) is known in the art:

Reaction Scheme 1

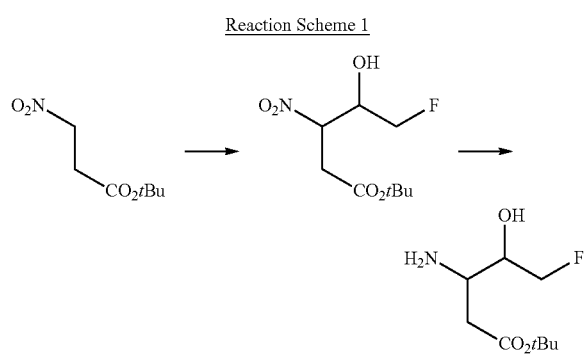

SUMMARY OF THE INVENTION

The present inventors have continued to study a compound that can be used as effective inhibitor of caspase, and a process for its preparation.

As a result, they discovered that the isoxazoline derivative having cyclic carboxylic acid hemiketal moiety according to the present invention has good caspase inhibition activity, and can be prepared in high purity by using crystallization-induced dynamic transformation, to complete the present invention.

Thus, one object of the present invention is to provide a compound of the following formula (1) with the structure of isoxazoline and cyclic carboxylic acid hemiketal moieties, and a novel process for effective preparation thereof.

Another object of the present invention is to provide an amine derivative of the following formula (4), an intermediate for the compound of the following formula (1), and a process for preparing it.

Another object of the present invention is to provide a pharmaceutical composition for treating inflammation or preventing apoptosis, comprising the compound of the following formula (1) and pharmaceutically acceptable carriers.

Another object of the present invention is to provide a method for treating inflammation or preventing apoptosis in a subject, comprising administering a therapeutically effective amount of the compound of the following formula (1) to the subject.

Another object of the present invention is to provide a use of the compound of the following formula (1) for the preparation of a medicament for treating inflammation or preventing apoptosis.

Another object of the present invention is to provide a crystalline form of the compound of the following formula (1) having good stability.

BRIEF DESCRIPTION OF THE DRAWINGS

FIG. 1 is X-ray diffraction spectrum of the crystalline form of the compound of formula (1) ($R^1$=isoquinolinyl, $R^2$=isopropyl) according to the present invention.

FIG. 2 is a graph showing stability test results of the crystalline form and amorphous form of the compound of formula (1) ($R^1$=isoquinolinyl, $R^2$=isopropyl) according to the present invention.

DISCLOSURE OF THE INVENTION

Some important terms used in the present invention can be defined as follows.

In the formulas and reaction schemes used in the present invention, alkyl refers to linear or branched alkyl group consisting of 1 to 8 carbon atoms, or cycloalkyl group consisting of 3 to 10 carbon atoms.

Also, aryl includes all of aromatic group, heteroaromatic group, and partially reduced derivatives thereof. Said aromatic group refers to 5- to 15-membered unsaturated hydrocarbons in simple or fused cyclic form, and said heteroaromatic group refers to aromatic groups having 1 to 5 hetero atoms selected from the group consisting of oxygen, sulfur and nitrogen.

Further, one or more hydrogens of said alkyl and said aryl may be substituted by other substituents. The examples of selectable substituents include acyl, amino, carboalkoxy, carboxy, carboxyamino, cyano, halo, hydroxy, nitro, thiol, alkyl, cycloalkyl, alkoxy, aryloxy, sulfoxy, guanido, etc.

The present invention relates to an isoxazoline derivative having cyclic carboxylic acid hemiketal moiety of the following formula (1) for use as caspase inhibitor:

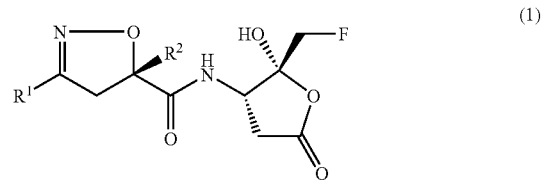

(1)

wherein
$R^1$ is alkyl or aryl, and
$R^2$ is alkyl.
Preferably,
$R^1$ is isoquinolinyl, quinolinyl or naphthyl, and
$R^2$ is methyl, ethyl, propyl or butyl.
More preferably, $R^1$ is isoquinolinyl, and $R^2$ is isopropyl.
The compound of formula (1) wherein $R^1$ is isoquinolinyl and $R^2$ is isopropyl can exist as a crystalline form showing the following X-ray diffraction pattern

| D (X) | Relative strength($I/I_0$) | 2θ Angle |
|---|---|---|
| 9.665 | 0.555 | 9.15 |
| 7.284 | 0.397 | 12.15 |
| 5.825 | 0.260 | 15.21 |
| 5.563 | 0.228 | 15.93 |
| 5.372 | 0.302 | 16.5 |
| 4.840 | 1.000 | 18.33 |
| 4.695 | 0.477 | 18.9 |
| 4.341 | 0.454 | 20.46 |
| 3.663 | 0.230 | 24.3 |
| 3.414 | 0.219 | 26.1 |

Also, the present invention relates to a process for preparing the compound of formula (1), comprising:

(a) activating a compound of the following formula (2), then reacting it with a compound of the following formula (4) to produce a compound of the following formula (13);

(b) hydrolyzing the compound of the following formula (13) to produce a compound of the following formula (14);

(c) deprotecting the compound of the following formula (14); and (d) carrying out crystallization-induced dynamic transformation;

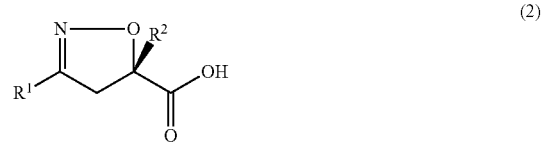

(2)

-continued

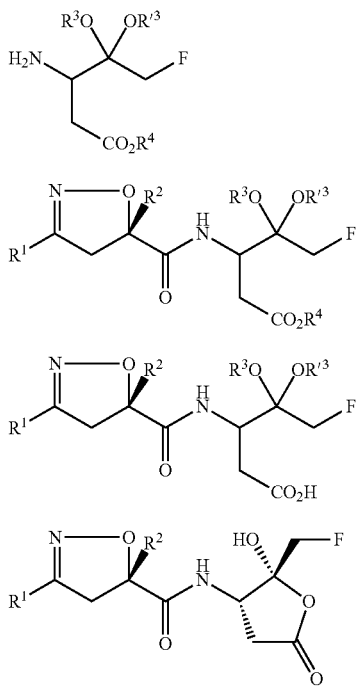

wherein,
R$^1$ is alkyl or aryl,
R$^2$ is alkyl,
R$^3$ and R$^{\prime 3}$ are each alkyl, or
R$^3$ and R$^{\prime 3}$ together with oxygen atom to which they are attached form heterocycle, and
R$^4$ is alkyl.
Preferably,
R$^1$ is isoquinolinyl, quinolinyl or naphthyl,
R$^2$ is methyl, ethyl, propyl or butyl,
R$^3$ and R$^{\prime 3}$ are each methyl, ethyl or propyl, or
R$^3$ and R$^{\prime 3}$ together with oxygen atom to which they are attached form dioxolane or dioxane, and
R$^4$ is methyl, ethyl, propyl or butyl.

Each step of the above preparation process of the compound of formula (1) may be described in more detail as follows.

As an activation reagent to activate the compound of formula (2) in the above step (a), it is preferable to use one selected from the group consisting of oxalyl chloride, trimethylacetyl chloride, phosphoryl tri-chloride, and thionyl chloride.

Also, it is preferable that the reaction in the step (a) is carried out in the presence of base selected from the group consisting of triethylamine, tri(n-butyl)amine, diisopropylethylamine, pyridine, 4-dimethylaminopyridine and 4-(4-methyl-piperidine-1-yl)-pyridine, and it is preferable that the base is used in an amount of 1.0 to 10.0 equivalents to the compound of formula (2).

Moreover, it is preferable that the reaction in the step (a) is carried out in one or more solvents selected from the group consisting of dichloromethane, chloroform, tetrahydrofuran, dimethoxyethane, dioxane and ethyl acetate.

On the other hand, it is preferable that the compound of formula (4) in the step (a) is used in an amount of 1.0 to 3.0 equivalents to the compound of formula (2).

It is preferable that the hydrolysis in the step (b) is carried out in the presence of base selected from the group consisting of lithium hydroxide (preferably, anhydrous or monohydrate crystalline), sodium hydroxide, potassium hydroxide and calcium hydroxide, and it is also preferable that the base is used in an amount of 0.1 to 10.0 equivalents to the compound of formula (13).

Moreover, it is preferable that the reaction in the step (b) is carried out in one or more solvents selected from the group consisting of methanol, ethanol, n-propanol, isopropanol, tetrahydrofuran, dimethoxyethane, dioxane and dichloromethane, or in a mixed solvent of the solvent selected from the above group and water.

It is preferable that the deprotection reaction in the step (c) is carried out in the presence of acid selected from the group consisting of hydrochloric acid, sulfuric acid and trifluoroacetic acid, and it is preferable that the acid is used in an amount of 0.1 to 20.0 equivalents to the compound of formula (14).

Also, it is preferable that the deprotection reaction in the step (c) is carried out in the presence or absence of solvent selected from dichloromethane or chloroform.

The crystallization-induced dynamic transformation reaction in the step (d) can be carried out by adding the compound of formula (1) as seed, or carried out in the presence of seed and a catalytic amount of base, wherein the base is preferably an amine selected from the group consisting of triethylamine, tri(n-butyl)amine, diisopropylethylamine, diisopropylamine, pyridine, 4-dimethylaminopyridine, 4-(4-methyl-piperidine-1-yl)-pyridine, optically active 1-phenylethylamine, and optically active 1-naphthylethylamine.

In the step (d), it is preferable to use said amine in an amount of 0.001 to 1.0 equivalent to the compound of formula (14), and more preferable to use 0.03 to 0.5 equivalent. If the amount of used amine is too little, the reaction rate becomes slower, and if the amount is too much, the yield of the compound of formula (1) is decreased.

Further, it is preferable that the crystallization-induced dynamic transformation reaction in the step (d) is carried out in one or more solvents selected from the group consisting of toluene, benzene, dichlorobenzene, tetrahydrofuran, dimethoxyethane, dioxane, ethyl acetate, dichloromethane, acetonitrile, methyl t-butylether, and diethylether.

Below, the process for preparing the compound of formula (1) according to the present invention will be explained in more detail with reference to Reaction Scheme 2.

The isoxazoline derivative of formula (2) having high optical activity is prepared according to the process disclosed in PCT/KR2004/002060 filed on Aug. 17, 2004 by the present applicant, and then combined with the compound of formula (4) to produce the compound of formula (13). Then, the compound of formula (13) is ester-hydrolyzed to produce the compound of formula (14), and the deprotection reaction of the ketal moiety of the compound of formula (14) is carried out to obtain a mixture of the compounds of formula (15) and formula (16), which is effectively transformed into the compound of formula (1) by selective dynamic crystallization.

In particular, if the mixture of the compounds of formula (15) and formula (16) is dissolved in organic solvent, and the seed of the compound of formula (1) is added to the solution, only the compound of formula (15) in the mixture is transformed into the compound of formula (1) to be isolated as solid.

Reaction Scheme 2

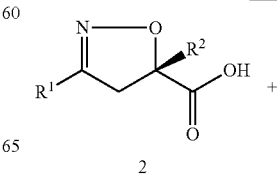

2

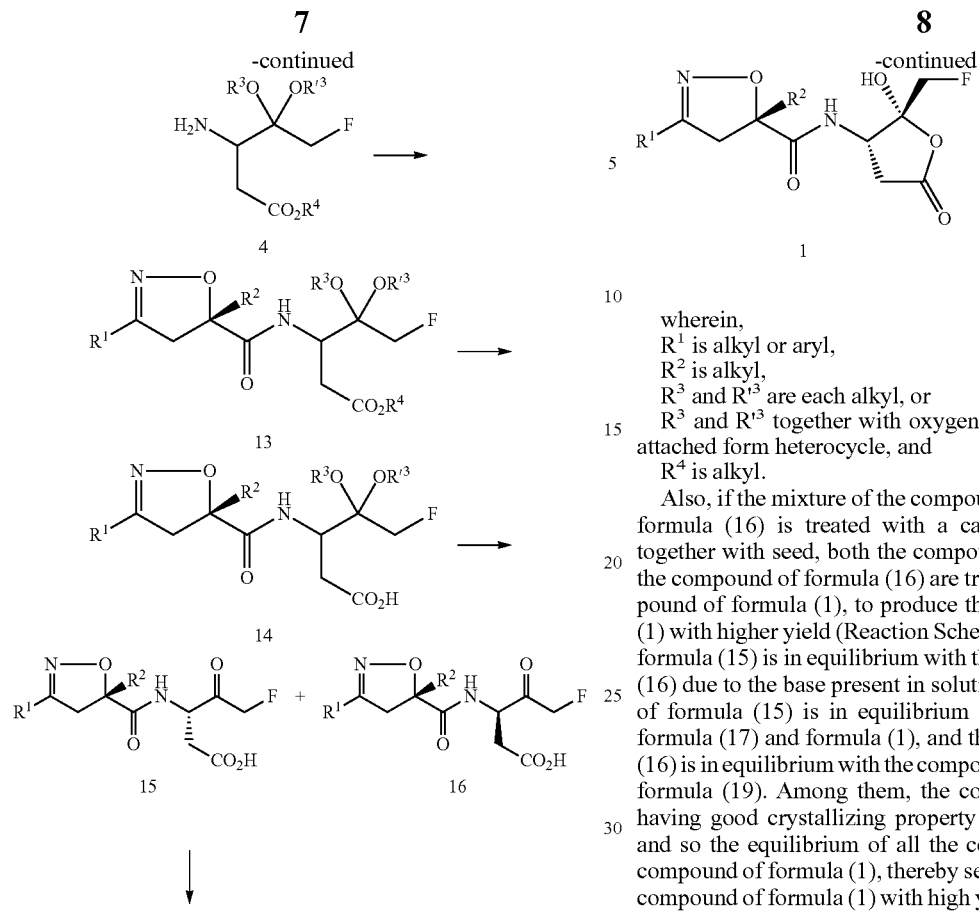

wherein,
R[1] is alkyl or aryl,
R[2] is alkyl,
R[3] and R'[3] are each alkyl, or
R[3] and R'[3] together with oxygen atom to which they are attached form heterocycle, and
R[4] is alkyl.

Also, if the mixture of the compounds of formula (15) and formula (16) is treated with a catalytic amount of base together with seed, both the compound of formula (15) and the compound of formula (16) are transformed into the compound of formula (1), to produce the compound of formula (1) with higher yield (Reaction Scheme 3). The compound of formula (15) is in equilibrium with the compound of formula (16) due to the base present in solution. Also, the compound of formula (15) is in equilibrium with the compounds of formula (17) and formula (1), and the compound of formula (16) is in equilibrium with the compounds of formula (18) and formula (19). Among them, the compound of formula (1) having good crystallizing property selectively precipitates, and so the equilibrium of all the compounds moves to the compound of formula (1), thereby selectively giving only the compound of formula (1) with high yield from the mixture of the compounds of formula (15) and formula (16).

Reaction Scheme 3

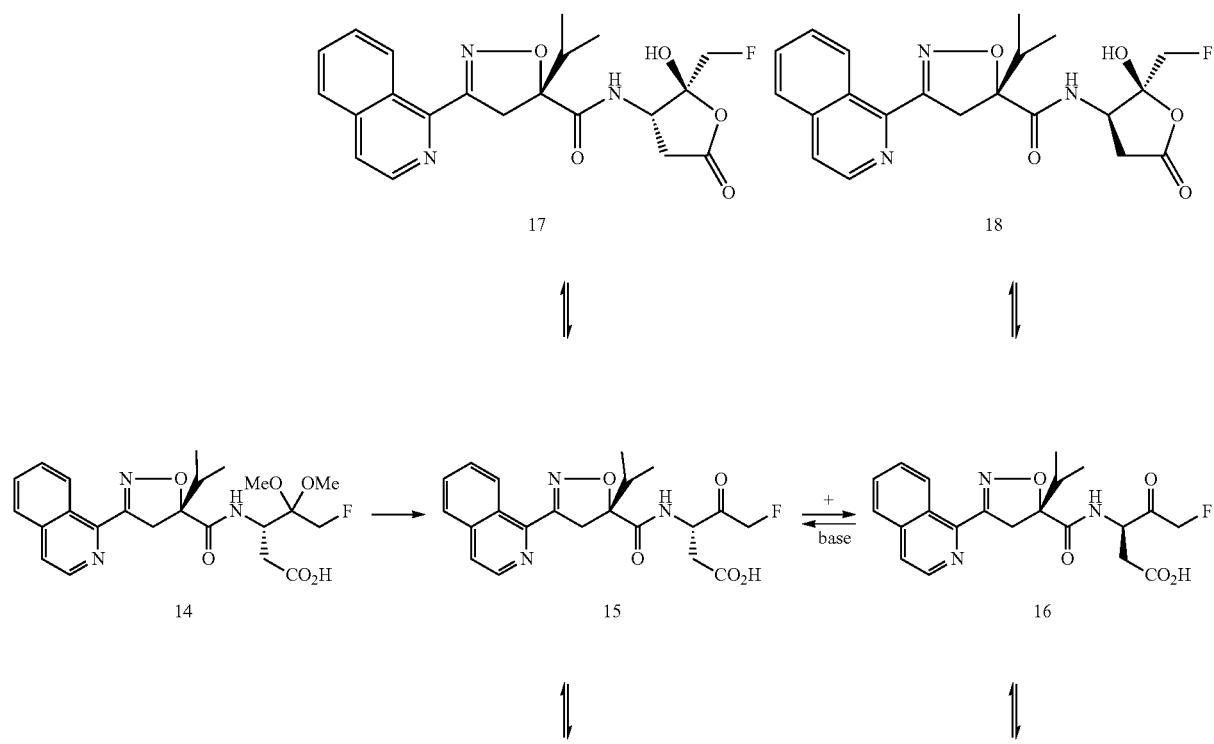

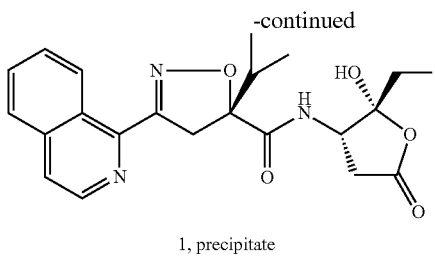
1, precipitate

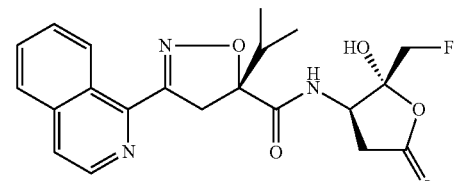
19

Also, the present invention relates to a compound of the following formula (4), an intermediate used for the preparation of the compound of formula (1):

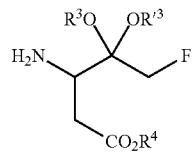
(4)

wherein $R^3$ and $R'^3$ are each alkyl, or $R^3$ and $R'^3$ together with oxygen atom to which they are attached form heterocycle, and $R^4$ is alkyl.

Preferably, $R^3$ and $R'^3$ are each methyl, ethyl or propyl, or $R^3$ and $R'^3$ together with oxygen atom to which they are attached form dioxolane or dioxane, and $R^4$ is methyl, ethyl, propyl or butyl.

Also, the present invention relates to a process for preparing the compound of formula (4), comprising:

(a) protecting and deprotecting a compound of the following formula (9) to produce a compound of the following formula (10);

(b) carrying out carbon-carbon coupling reaction of the compound of formula (10) to produce a compound of the following formula (11);

(c) reacting the compound of formula (11) with benzyl amine, and reducing it to produce a compound of the following formula (12); and (d) hydrogenating the compound of formula (12);

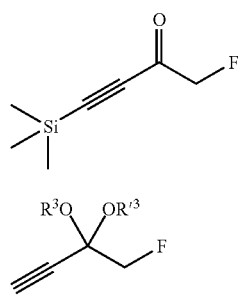

(9)

(10)

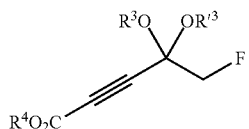
(11)

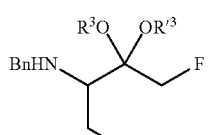
(12)

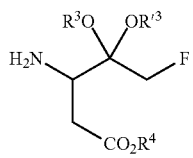
(4)

wherein $R^3$ and $R'^3$ are each alkyl, or $R^3$ and $R'^3$ together with oxygen atom to which they are attached form heterocycle, and $R^4$ is alkyl.

Preferably, $R^3$ and $R'^3$ each are methyl, ethyl or propyl, or $R^3$ and $R'^3$ together with oxygen atom to which they are attached form dioxolane or dioxane, and $R^4$ is methyl, ethyl, propyl or butyl.

The above process for preparing the compound of formula (4) will be more specifically described below.

In the step (a), it is preferable that the compound of formula (9) is protected by using trimethylorthoformate or triethylorthoformate, and the deprotection reaction is carried out in the presence of base selected from sodium hydroxide, potassium hydroxide, sodium carbonate, and sodium hydrogen carbonate. Further, it is preferable that the base in the above deprotection reaction is used in an amount of 1.0 to 2.0 equivalents to the compound of formula (9).

Also, it is preferable that the protection reaction in the step (a) is carried out in methanol or ethanol solvent, and the deprotection reaction is carried out in one or more solvents selected from the group consisting of methanol, ethanol, dichloromethane, chloroform, and water.

Also, it is preferable that the reaction in the step (b) is carried out by using ethylchloroformate or methylchloroformate in the presence of base selected from n-butyllithium, lithiumdiisopropylamine or lithiumhexamethyldisilazide, and the base is used in 0.5 to 3.0 equivalents to the compound of formula (10), and said ethylchloroformate or methylchloroformate is used in 0.5 to 3.0 equivalents to the compound of formula (10).

Also, it is preferable that the reaction in the step (b) is carried out in a solvent selected from the group consisting of tetrahydrofuran, ethyl ether, and methyl-t-butyl ether.

It is preferable that the reduction reaction in the step (c) is carried out by using acetic acid and sodium borohydride, and said sodium borohydride is used in 1.0 to 5.0 equivalents to the compound of formula (11), and said acetic acid is used in 1.0 to 20.0 equivalents to the compound of formula (11).

Also, it is preferable that said benzyl amine in the step (c) is used in 1.0 to 10.0 equivalents to the compound of formula (11).

Further, it is preferable that the reaction in the step (c) is carried out in the presence or absence of solvent selected from ethyl acetate, tetrahydrofuran, ethylether and methyl-t-butyl ether, and may be carried out as one-pot reaction, if desired.

It is preferable that the reaction in the step (d) is carried out in the presence of metal catalyst, more preferably palladium family catalyst or Raney nickel family catalyst. Specifically, palladium family catalyst having 1 to 20 wt % of palladium (Pd) or Raney nickel family catalyst having 1 wt % or more of Raney nickel, supported on a carrier selected from the group consisting of carbon, silica and alumina, may be used in an amount of 0.01 to 10 wt % based on its metal component to the compound of formula (12).

Also, it is preferable that the reaction in the step (d) is carried out in one or more solvents selected from the group consisting of methanol, ethanol, n-propanol, isopropanol, tetrahydrofuran, dimethoxyethane, dioxane, ethyl acetate and dichloromethane.

Further, it is preferable that the hydrogenation reaction in the step (d) is carried out at a temperature of 0 to 50° C. and under a hydrogen pressure of 1 to 100 atm.

The present inventors have developed a novel process for preparing the compound of formula (4), an intermediate for the compound of formula (1), with higher yield, as illustrated in the following Reaction Scheme 4.

Reaction Scheme 4

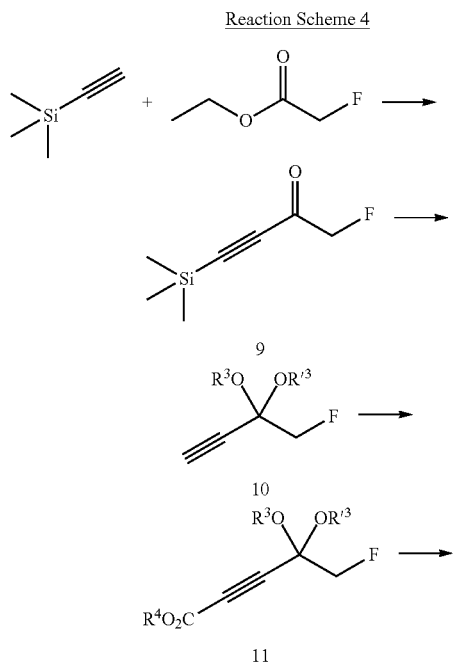

wherein
$R^3$ and $R'^3$ are each alkyl, or
$R^3$ and $R'^3$ together with oxygen atom to which they are attached form heterocycle, and
$R^4$ is alkyl.

Also, the present invention relates to a pharmaceutical composition for treating inflammation or preventing apoptosis, comprising the compound of the above defined formula (1) and pharmaceutical acceptable carriers, specifically a pharmaceutical composition for treating dementia, cerebral stroke, brain impairment due to AIDS, diabetes, gastric ulcer, cerebral injury by hepatitis virus, hepatic diseases by hepatitis virus, acute hepatitis, fulminant hepatic failure, hepatocirrhosis, sepsis, organ transplantation rejection, rheumatoid arthritis, or cardiac cell necrosis due to ischemic cardiac diseases.

Also, the present invention relates to a method for treating inflammation or preventing apoptosis in a subject, comprising administering a therapeutically effective amount of the compound of the above defined formula (1) to the subject, specifically a method for treating dementia, cerebral stroke, brain impairment due to AIDS, diabetes, gastric ulcer, cerebral injury by hepatitis virus, hepatic diseases by hepatitis virus, acute hepatitis, fulminant hepatic failure, hepatocirrhosis, sepsis, organ transplantation rejection, rheumatoid arthritis, or cardiac cell necrosis due to ischemic cardiac diseases.

Also, the present invention relates to a use of the compound of the above defined formula (1) for the manufacture of a medicament for treating inflammation or preventing apoptosis, specifically a medicament for treating dementia, cerebral stroke, brain impairment due to AIDS, diabetes, gastric ulcer, cerebral injury by hepatitis virus, hepatic diseases by hepatitis virus, acute hepatitis, fulminant hepatic failure, hepatocirrhosis, sepsis, organ transplantation rejection, rheumatoid arthritis, or cardiac cell necrosis due to ischemic cardiac diseases.

The compound of formula (1) according to the present invention may be formulated into various pharmaceutical forms for administration purpose. To prepare the pharmaceutical composition according to the present invention, an effective amount of the compound of formula (1) is mixed with a pharmaceutical acceptable carrier that may take a wide variety of forms depending on the formulation to be prepared.

The compound of formula (1) may be formulated as a parenteral injection, or percutaneous or oral preparation depending on its application purpose. It is especially advantageous to formulate the composition in a unit dosage form for ease of administration and uniformity of dosage.

For the oral preparation, any usual pharmaceutical carrier may be used. For example, water, glycols, oils, alcohols and the like may be used for oral liquid preparations such as suspensions, syrups, elixirs and solutions; or starches, sugars, kaolin, lubricants, binders, disintegrating agents and the like may be used for solid preparations such as powders, pills, capsules and tablets. Due to their ease of administration, tablets and capsules are the most advantageous dosage unit forms. It is also desirable for tablets and pills to be formulated into enteric-coated preparation.

For the parenteral preparation, sterile water is usually used as the carrier, though other ingredients such as solubility aids may be used. Injections, for example, sterilized aqueous or oily suspension for injection, can be prepared according to the known procedure using suitable dispersing agent, wetting agent, or suspending agent. Solvents that can be used for preparing injections include water, Ringer's fluid, and isotonic NaCl solution, and sterilized fixing oil may also be conveniently used as the solvent or suspending media. Any non-stimulative fixing oil including mono-, di-glyceride may be used for this purpose. Fatty acid such as oleic acid may also be used for injections.

For the percutaneous preparation, the carrier may include a penetration enhancing agent and/or a suitable wetting agent, optionally combined with suitable additives having no significant skin irritation. Said additives may facilitate the administration through the skin and/or may assist preparation of a desired composition. These percutaneous preparations are administered via various manners, e.g., as a transdermal patch, a spot-on, or an ointment.

When the compound of formula (1) is used for clinical purpose, it is preferably administered to the subject patient in an amount ranging from 0.1 to 100 mg per kg of body weight a day. The total daily dosage may be administered once or over several times. However, specific administration dosage for an individual patient can be varied with specific compound used, body weight, sex, hygienic condition, or diet of the subject patient, time or method of administration, excretion rate, mixing ratio of agent, severity of disease to be treated, etc.

Hereinafter, the present invention will be described in more detail with reference to the following Examples, but the scope of the present invention should not be construed to be limited thereby in any manner.

Preparation Example 1

1-Fluoro-4-trimethylsilanyl-3-butyn-2-one (9)

49.1 g (499 mmol) of trimethylsilyl acetylene was dissolved in 250 mL of anhydrous tetrahydrofuran, and the inner temperature was lowered to about −55° C., and then 210 mL (525 mmol) of 2.5 M n-BuLi in n-hexane was added thereto over about 25 minutes with maintaining the inner temperature below −30° C. After stirring for about 40 minutes, 52.9 g (499 mmol) of ethyl fluoroacetate was added to the reaction mixture over 5 minutes with maintaining the inner temperature below −25° C., and then 74.4 g (524 mmol) of $BF_3.OEt$ was added thereto over 15 minutes with maintaining the inner temperature −55° C. to −65° C. After finishing the addition, the reaction mixture was stirred at 20° C. for 2 hours, and 250 mL of 10% ammonium chloride aqueous solution was added thereto to finish the reaction. The organic layer was separated, and the aqueous layer was extracted with 200 mL of ethylacetate. The combined organic phase was washed with 250 mL of brine, and concentrated under reduced pressure. The residue was distilled under vacuum at 10 mbar and 68° C. to give the compound of formula (9) (67.3 g, 85%) as clear oil.

$^1$H NMR (500 MHz, $CDCl_3$): 4.90 (d, J=47.1 Hz, 2H), 0.26 (s, 9H)

$^{13}$C NMR (125 MHz, $CDCl_3$): 181.0 (d, J=21.5 Hz), 104.0, 98.1, 84.8 (d, J=187 Hz)

Preparation Example 2

4-Fluoro-3,3-dimethoxy-1-butyne (10, $R^3$, $R^{i3}$=methyl)

33.6 g (316 mmol) of trimethyl orthoformate and 6.0 g (31.5 mmol) of p-TsOH—$H_2O$ together with 50.0 g (316 mmol) of the compound of formula (9) obtained from the Preparation Example 1 were put into 260 mL of methanol, and stirred at reflux temperature (inner temperature 60~64° C.) for about 6 hours. The reaction mixture was concentrated under reduced pressure to remove about 130 mL of solvent, and was diluted with 260 mL of methylene chloride. 130 mL of 10% aqueous sodium hydrogen carbonate solution was added thereto and layer-separated, and the water layer was extracted by using 130 mL of methylene chloride. The combined organic layer was concentrated under reduced pressure to give 4-fluoro-3,3-dimethoxy-1-trimethylsilylbutyne (59.0 g, 92%) as an intermediate, a precursor compound of the object compound (10). This compound was used in the next reaction without further purification.

$^1$H NMR (500 MHz, $CDCl_3$): 4.38 (d, J=47.1 Hz, 2H), 3.40 (s, 6H), 0.20 (s, 9H)

59.0 g (289 mmol) of 4-fluoro-3,3-dimethoxy-1-trimethylsilylbutyne, a precursor compound of the object compound (10) obtained from the above, was dissolved in 280 mL of methylene chloride, treated with 59 mg (0.183 mmol) of tetra-n-butyl ammoniumbromide and 347 mL (347 mmol) of 1 N sodium hydroxide aqueous solution, and stirred for about 2 hours. The organic layer was separated, and the aqueous layer was extracted with 110 mL of methylene chloride. The combined organic layer was washed with 110 mL of brine, and concentrated under reduced pressure to give the object compound (10, $R^3$, $R^{i3}$=methyl; 40.9 g, quantitative yield). This compound was used in the next reaction without further purification.

$^1$H NMR (500 MHz, $CDCl_3$): 4.42 (d, J=47.1 Hz, 2H), 3.42 (s, 6H), 2.64 (s, 1H)

$^{13}$C NMR (125 MHz, $CDCl_3$): 96.1 (d, J=20.3 Hz), 82.9 (d, J=180 Hz), 77.5, 75.5, 51.0

Preparation Example 3

Ethyl 5-fluoro-4,4-dimethoxy-2-pentynoate (11, $R^3$, $R^{i3}$=methyl, $R^4$=ethyl)

A solution of 40.9 g (405 mmol) of diisopropylamine in 270 mL of tetrahydrofuran was cooled to 0° C., and 112 g (405 mmol) of 2.5 M n-BuLi in n-hexane was added thereto over about 1 hour with maintaining the inner temperature below 14° C. The reaction mixture was stirred at 0° C. for about 30 minutes, and the temperature was adjusted to −78° C. A solution of 41.0 g (311 mmol) of the compound obtained from the above Preparation Example 2 (10, $R^3$, $R^{i3}$=methyl) dissolved in 160 mL of tetrahydrofuran was added to the reaction mixture over about 2 hours with maintaining the inner temperature below −40° C., and then 60.4 g (557 mmol) of ethyl chloroformate was added thereto over about 1 hour with maintaining the inner temperature below −40° C., and further the reaction mixture was stirred at 0° C. for about 2 hours. 250 mL of 10% ammonium chloride aqueous solution was added to the reaction mixture to finish the reaction, and the organic layer was separated. The aqueous layer was extracted with 100 mL of ethyl acetate, and the combined organic layer was washed with 100 mL of brine and concentrated under reduced pressure to give the crude object compound (11, $R^3$, $R^{i3}$=methyl, $R^4$=ethyl; 95.0 g, calculated yield 70%). This compound was used in the next reaction without further purification $^1$H NMR (500 MHz, $CDCl_3$): 4.45 (d, J=46.5 Hz, 2H), 4.25 (q, J=7.1 Hz, 2H), 3.43 (s, 6H), 1.31 (t, J=7.3 Hz, 3H)

Preparation Example 4

Ethyl 3-(benzylamino)-5-fluoro-4,4-dimethoxypentanoate (12, $R^3$, $R^{i3}$=methyl, $R^4$=ethyl)

88 g (431 mmol) of the crude compound obtained from the above Preparation Example 3 (11, $R^3$, $R^{i3}$=methyl, $R^4$=ethyl) was dissolved in 430 mL of methyl-t-butyl ether (MTBE), and the temperature was adjusted to 0° C. 31.4 g (293 mmol) of benzylamine was added to the reaction mixture, stirred at 20° C. for about 1 hour, and diluted with 450 mL of methyl-t-butyl ether. Again, the temperature of the reaction mixture was adjusted to 0° C., 33 g (873 mmol) of NaBH$_4$ was added to the reaction mixture, and then 259 g (4320 mmol) of acetic acid was added thereto over about 30 minutes. The reaction mixture was maintained at 0° C., and 880 mL (2640 mmol) of 3 N sodium hydroxide aqueous solution was slowly added thereto over about 2 hours. The organic layer was separated, and the separated organic layer was washed with 880 mL of 10% ammonium chloride aqueous solution, and then 880 mL of 1 N hydrochloric acid aqueous solution was added thereto. The aqueous layer was separated, washed with 400 mL of methyl-t-butyl ether, and basified by using 246 mL of 10 N sodium hydroxide aqueous solution, and extracted with 700 mL×2 of methyl-t-butyl ether. The combined organic layer was washed with 400 mL of brine, and concentrated under reduced pressure to give the object compound [12, $R^3$, $R^{i3}$=methyl, $R^4$=ethyl; 60.0 g, 44%, and 65% from the compound of formula (10)]. This compound was used in the next reaction without further purification $^1$H NMR (400 MHz, CDCl$_3$): 7.35-7.21 (m, 5H), 4.53 (2dd, J=46.8, 10.4 Hz, 2H), 4.13 (q, J=7.2 Hz, 2H), 3.80 (2d, J=12.8 Hz, 2H), 3.53 (dd, J=8.4, 4.0 Hz, 1H), 3.30 (s, 3H), 3.22 (s, 3H), 2.79 (dd, J=15.6, 3.6 Hz, 1H), 2.40 (ddd, J=15.6, 8.0, 1.6 Hz, 1H), 1.25 (t, J=7.2 Hz, 3H)

Example 1

Ethyl 3-amino-5-fluoro-4,4-dimethoxypentanoate (4, $R^3$, $R^{i3}$=methyl, $R^4$ ethyl)

18.3 g (58.5 mmol) of the compound obtained from the above Preparation Example 4 (12, $R^3$, $R^{i3}$=methyl, $R^4$=ethyl) was dissolved in 180 mL of ethanol, and debenzylation was carried out by using activated carbon 5% palladium catalyst (5% Pd/C) at the hydrogen pressure of 50 psi for about 4 hours. The reaction mixture was filtered through 5.0 g of Cellite pad, and washed with 90 mL of ethanol, and the filtrate was concentrated under reduced pressure to give the object compound (4, 12.8 g, 98%). This compound was used in the next step without any purification.

$^1$H NMR (500 MHz, CDCl$_3$): 4.53 (2dd, J=46.5, 10.4 Hz, 2H), 4.14 (q, J=7.3 Hz, 2H), 3.57 (dd, J=11.0, 1.9 Hz, 1H), 3.29 (d, J=11.7 Hz, 6H), 2.73 (dd, J=16.5, 2.5 Hz, 1H), 2.36 (ddd, J=16.5, 10.4, 2.5 Hz, 1H), 1.25 (t, J=7.3 Hz, 3H)

Preparation Example 5

5-fluoro-3-[((R)-5-isopropyl-3-(1-isoquinolinyl)-4,5-dihydro-isoxazole-5-carbonyl)-amino]-4,4-dimethoxy-pentanoic acid ethyl ester (13, $R^1$=1-isoquinolinyl, $R^2$=isopropyl, $R^3$, $R^{i3}$=methyl, $R^4$=ethyl)

15.5 g (54.5 mmol) of (5R)-5-isopropyl-3-(1-isoquinolinyl)-4,5-dihydro-5-isoxazole carboxylic acid (2, $R^1$=1-isoquinolinyl, $R^2$=isopropyl) was dissolved in 150 mL of methylene chloride, the temperature was adjusted to 0° C., and then 7.1 mL (81.7 mmol) of oxalyl chloride and 0.2 mL (2.6 mmol) of DMF were added thereto with maintaining the inner temperature below 12° C. The reaction mixture was stirred at 20° C. for about 2 hours, and concentrated under reduced pressure. The reaction mixture was dissolved in 150 mL of methylene chloride, the temperature was adjusted to 0° C., triethylamine was added thereto, and a solution of 12.8 g (57.4 mmol) of the compound obtained from Example 1 (4, $R^3$, $R^{i3}$=methyl, $R^4$=ethyl) dissolved in 30 mL of methylene chloride was slowly added thereto over 20 minutes. The reaction mixture was stirred at 25° C. for 1.5 hours, a mixed solution of 120 mL of 10% sodium hydrogen carbonate aqueous solution and 60 mL of 1 N sodium hydroxide aqueous solution was added thereto to finish the reaction. The organic layer was separated, and the aqueous layer was extracted with 150 mL×3 of methylene chloride. The combined organic layer was concentrated under reduced pressure to give the object compound (13, $R^1$=1-isoquinolinyl, $R^2$=isopropyl, $R^3$, $R^{i3}$=methyl, $R^4$=ethyl; 30.1 g, quantitative yield). This compound was used in the next step without any purification.

$^1$H NMR (500 MHz, CDCl$_3$): 9.12 (q, 1H), 8.53 (m, 1H), 7.85-7.25 (m, 4H), 4.80 (m, 1H), 4.54-4.34 (m, 2H), 4.14 (q, J=7.4 Hz, 2H), 3.99 (2d, J=18.4 Hz, 1H), 3.81 (m, 1H), 3.78 (2d, J=8.6 Hz, 1H), 3.33 (d, 3H), 3.20 (d, 3H), 2.75 (m, 3H), 2.53 (m, 1H), 2.39 (heptet, J=6.7 Hz, 1H), 1.27 (t, J=7.4 Hz, 1.5H), 1.07 (m, 6H), 0.97 (t, J=7.4 Hz, 1.5H)

Preparation Example 6

5-Fluoro-3-[((R)-5-isopropyl-3-(1-isoquinolinyl)-4,5-dihydro-isoxazole-5-carbonyl)-amino]-4,4-dimethoxy-pentanoic acid (14, $R^1$=1-isoquinolinyl, $R^2$=isopropyl, $R^3$, $R^{i3}$=methyl)

30.1 g (61.6 mmol) of the compound obtained from the above Preparation Example 5 (13, $R^1$=1-isoquinolinyl, $R^2$=isopropyl, $R^3$, $R^{i3}$=methyl, $R^4$=ethyl) together with 7.76 g (185 mmol) of lithium hydroxide monohydrate were dissolved in a mixed solvent of 168 mL of tetrahydrofuran and 42 mL of water, and stirred at about 40° C. for 4 hours. The reaction mixture was concentrated under reduced pressure to remove tetrahydrofuran in the solvent, 180 mL of 1 N sodium hydroxide aqueous solution was added thereto, and the mixture was washed with 120 mL×2 of toluene. The aqueous layer was acidified with 66 mL of 6 N hydrochloric acid aqueous solution, and extracted with 150 mL×3 of methylene chloride, and the combined organic layer was concentrated under reduced pressure to give the object compound (14, $R^1$=1-isoquinolinyl, $R^2$=isopropyl, $R^3$, $R^{i3}$=methyl; 25.4 g, 89%). This compound was used in the next step without any purification.

$^1$H NMR (400 MHz, CDCl$_3$): 9.10-8.92 (m, 1H), 8.52 (m, 1H), 7.86-7.13 (m, 4H), 4.77 (m, 1H), 4.54-4.34 (m, 2H), 3.95 (2d, J=8.0 Hz, 1H), 3.75 (2d, J=18.4 Hz, 1H), 3.35-3.16 (2d, 6H), 2.78 (2dd, J=16.0, 4.4 Hz 1H), 2.54 (m, 1H), 2.39 (m, 1H), 2.35 (s, 1H), 1.06 (m, 6H)

Example 2

(4S,5S)-5-fluoromethyl-5-hydroxy-4-({[(5R)-5-isopropyl-3-(1-isoquinolinyl)-4,5-dihydro-5-isoxazolyl]carbonyl}amino)-2-dihydrofuranone (1, $R^1$=1-isoquinolinyl, $R^2$=isopropyl)

17.0 g (36.9 mmol) of the compound obtained from the above Preparation Example 6 (14, $R^1$=1-isoquinolinyl, $R^2$=isopropyl, $R^3$, $R'^3$=methyl) and 6.6 mL (110 mmol) of acetic acid were dissolved in 123 mL (738 mmol) of 6 N hydrochloric acid aqueous solution, and stirred for about 4 hours. The inner temperature of the reaction mixture was adjusted to 0° C., and 150 mL of ethyl acetate was added thereto. 220 mL (660 mmol) of 3 N sodium hydroxide aqueous solution was slowly added to adjust the pH to about 3. The organic layer was separated, and the aqueous layer was extracted with 150 mL×2 of ethyl acetate. The combined organic phase was washed with 100 mL of brine, and concentrated under reduced pressure. The residue was diluted with 50 mL of toluene, and concentrated again under reduced pressure to give a mixture of the compounds of formula (15) and formula (16) ($R^1$=1-isoquinolinyl, $R^2$=isopropyl) (15.4 g, quantitative yield, chemical purity: 87.0%).

$^1$H NMR (500 MHz, DMSO-d6): 8.99 (m, 1H), 8.65 (m, 1H), 8.19-7.78 (m, 4H), 5.15 (m, 1.5H), 4.77 (m, 1H), 4.42 (m, 0.5H), 3.91 (2d, J=17.6 Hz, 1H), 3.74 (m, 1H), 2.99 (m, 0.2H), 2.82 (m, 1H), 2.63 (m, 0.8H), 2.33 (m, 1H), 0.97 (m, 6H)

To 146 mL of toluene was added 14.6 g (35.2 mmol) of the mixture of the compounds of formula (15) and formula (16) ($R^1$=1-isoquinolinyl, $R^2$=isopropyl) (chemical purity: 87.0%), and the mixture was heated up to 100° C. to dissolve it completely. Then, 14 mg of seed of the object compound (1, $R^1$=1-isoquinolinyl, $R^2$=isopropyl) was added thereto, the temperature was slowly lowered to 20° C., and the reaction mixture was stirred to produce solid. 0.25 mL (1.8 mmol) of diisopropylamine was added thereto, and stirred at 20° C. for about 2 weeks, to confirm that the ratio between the compound of formula (15) and the compound of formula (16) ($R^1$=1-isoquinolinyl, $R^2$=isopropyl) is 92.8:7.2 by HPLC. The reaction mixture was concentrated under reduced pressure to remove toluene, 88 mL of ethyl acetate was added thereto, and the mixture was heated up to 65° C. to dissolve it completely. Then, 88 mL of normal hexane was added thereto, and the temperature was slowly lowered and stirred at about 20° C. for 2 days. The resulting solid was filtered, and washed with a mixed solution of 15 mL of ethyl acetate and 15 ml of normal hexane. After drying the solid with nitrogen, the object compound, a white solid (1, $R^1$=1-isoquinolinyl, $R^2$=isopropyl), was obtained in 54.7% of yield from the compound of formula (2) (8.0 g, chemical purity 98.6%).

Solid NMR data of the crystalline form was obtained by using VACP MAS (variable amplitude cross polarization magic angle spinning) at 9 kH spinning rate.

$^1$H NMR (CDCl$_3$): 9.02 (bs, 1H), 8.54 (d, J=5.5 Hz, 1H), 7.85 (d, J=7.95 Hz, 1H), 7.70 (m, 3H), 7.60 (bs, 1H), 4.86 (bs, 1H), 4.2-5.2 (bs, 2H), 4.05 (b, J=19.0 Hz, 1H), 3.78 (b, J=19.0 Hz, 1H), 2.7-3.1 (bm, 2H), 2.40 (m, 1H). 1.08 (dd, J=6.7, 4.9 Hz, 6H)

$^{13}$C NMR (CDCl$_3$): 173.8, 172.4, 160.2, 147.6, 141.7, 136.8, 130.7, 129.0, 127.4, 127.3, 126.8, 122.9, 92.3, 82.7 (d, J=215 Hz), 48.9 (b), 44.6, 34.4, 33.9, 17.7, 16.3

$^{13}$C NMR (solid): 176.4, 171.8, 160.3, 150.2, 139.5, 137.5, 132.3 (2C), 127.7 (3C), 123.0, 104.3, 94.1, 86.4, 48.8, 42.9, 32.7 (2C), 19.6, 15.4

Mass (ESI): 416.14 (M+1)

$[\alpha]_D^{25}$=+3.2(c=1.0, acetonitrile)

Experimental Example 1

Stability Test

As shown in FIG. 2, as a result of the stability test on the amorphous form and crystalline form of the compound of formula (1) ($R^1$=1-isoquinolinyl, $R^2$=isopropyl), it was observed that 50% of the amorphous form was destroyed after 28 days under severe condition (60° C.), but the quantitative amount of the crystalline form was not decreased at all under the same condition (60° C.) even after 28 days. Therefore, it should be understood that the crystalline form has better stability than the amorphous form enough to be used for the composition of inhibitor or therapeutic agent.

Experimental Example 2

Treatment Effect on LPS-Induced Acute Hepatitis in Mice

Step 1: Preparation of Blood Sample

Male Balb/c mice (6 weeks, Charles River Laboratory, Osaka, Japan) were bred up at 22° C. under 55% of relative humidity, with changing night/day per 12 hours. Feed and water were supplied without limit. LPS (lipopolysaccharide) and D-galactosamine were dissolved in the concentrations of 0.4 mg/mL and 280 mg/mL, respectively, in pyrogen-free saline, and mixed in the ratio of 1:1. The solution was injected into the mice in the amount of 5 ml/kg. Immediately after the injection of LPS and D-galactosamine, vehicle wherein the test compound is dissolved (a mixture consisting of PEG400: ethanol:Tween80 in 15:7.5:2.5 is ⅕ diluted with saline) or vehicle alone was injected to the test animal. Blood samples were obtained from the mice hearts 8 hours after the drug injection.

Step 2: Blood Plasma Aminotransferase Activity Assay

Blood plasma ALT activity of the blood samples obtained in the Step 1 was measured by using ALT assay kit (Asan pharmaceutical company) according to the manufacturer's protocol. It was observed that administration of LPS and D-galactosamine rapidly increased ALT activity in blood plasma, and the test material inhibited such increased enzymatic activity in a dose-dependent manner. Based on these results, $ED_{50}$ value for each test material was calculated by using Prism software (GraphPad Co.).

Experimental Example 3

Treatment Effect On Fas Antibody-Induced Acute Hepatitis in Mice

Male Balb/c mice (6 weeks, Charles River Laboratory, Osaka, Japan) were bred up at 22° C. under 55% of relative humidity, with changing night/day per 12 hours. Feed and water were supplied without limit. Fas antibody was dissolved in the concentration of 30 ug/mL in pyrogen-free saline, and the solution was injected into the mice in the amount of 5 ml/kg. Immediately after injection of Fas antibody, vehicle wherein the test compound is dissolved (a mixture consisting of PEG400:ethanol:Tween80 in 15:7.5:2.5 is ⅕ diluted with saline) or vehicle alone was injected to the test animal. Blood samples were obtained from the mice hearts 8 hours after the drug injection. $ED_{50}$ value for the obtained blood sample was calculated by using the above test method. The following Table 1 shows the pharmacological effect test results in acute hepatitis model according to administration route of the compound of formula (1) obtained from the above Examples 2 and 3.

TABLE 1

| Model 1 | Administration route | $ED_{50}$ (mg/kg) | 95% confidence interval (mg/kg) |
|---|---|---|---|
| LPS/D-Gln | Intravenous administration | 0.015 | 0.002~0.111 |
|  | Oral administration | 0.02 | 0.003~0.118 |

TABLE 1-continued

| Model 1 | Administration route | ED$_{50}$ (mg/kg) | 95% confidence interval (mg/kg) |
|---|---|---|---|
| Fas antibody | Intravenous administration | 0.003 | 0.001~0.006 |
| | Oral administration | 0.018 | 0.013~0.026 |

INDUSTRIAL APPLICABILITY

The isoxazoline derivative having cyclic carboxylic acid hemiketal of formula (1) according to the present invention has excellent caspase inhibitory activity and excellent stability. In addition, the process according to the present invention produces only one diastereoisomer of high purity by using crystallization-induced dynamic transformation. Further, if amine derivative having ketal according to the present invention is used as intermediate, a person skilled in the art can easily prepare the isoxazoline derivative having cyclic carboxylic acid hemiketal without additional purification.

What is claimed is:

1. A compound of formula (1):

(1)

wherein
$R^1$ is alkyl or aryl, selected from isoquinolinyl, quinolinyl or naphthyl and
$R^2$ is alkyl.

2. The compound of claim 1, wherein
$R^1$ is isoquinolinyl, quinolinyl or naphthyl, and
$R^2$ is methyl, ethyl, propyl or butyl.

3. The compound of claim 2, wherein
$R^1$ is isoquinolinyl, and $R^2$ is isopropyl.

4. A process for preparing a compound of formula (1), comprising:
(a) activating a compound of formula (2), then reacting it with a compound of formula (4) to produce a compound of formula (13);
(b) hydrolyzing the compound of formula (13) to produce a compound of formula (14);
(c) deprotecting the compound of formula (14); and
(d) carrying out crystallization-induced dynamic transformation;

(2)

(4)

(13)

(14)

(1)

wherein,
$R^1$ is alkyl or aryl,
$R^2$ is alkyl,
$R^3$ and $R'^3$ are each alkyl, or
$R^3$ and $R'^3$ together with oxygen atom to which they are attached form heterocycle, and
$R^4$ is alkyl.

5. The process of claim 4, wherein
$R^1$ is isoquinolinyl, quinolinyl or naphthyl,
$R^2$ is methyl, ethyl, propyl or butyl,
$R^3$ and $R'^3$ are each methyl, ethyl or propyl, or
$R^3$ and $R'^3$ together with oxygen atom to which they are attached form dioxolane or dioxane, and
$R^4$ is methyl, ethyl, propyl or butyl.

6. The process of claim 4, wherein the compound of formula (2) in the step (a) is activated by an activation reagent selected from the group consisting of oxalyl chloride, trimethylacetyl chloride, phosphoryl tri-chloride and thionyl chloride.

7. The process of claim 4, wherein the reaction in the step (a) is carried out in the presence of base selected from the group consisting of triethylamine, tri(n-butyl)amine, diisopropylethylamine, pyridine, 4-dimethylaminopyridine and 4-(4-methyl-piperidine-1-yl)-pyridine.

8. The process of claim 4, wherein the hydrolysis in the step (b) is carried out in the presence of base selected from the group consisting of lithium hydroxide, sodium hydroxide, potassium hydroxide and calcium hydroxide.

9. The process of claim 4, wherein the deprotection reaction in the step (c) is carried out in the presence of acid selected from the group consisting of hydrochloric acid, sulfuric acid and trifluoroacetic acid.

10. The process of claim 4, wherein the deprotection reaction in the step (c) is carried out in the presence or absence of solvent selected from dichloromethane or chloroform.

11. The process of claim 4, wherein the crystallization-induced dynamic transformation reaction in the step (d) is carried out by adding the compound of formula (1) as seed.

12. The process of claim 11, wherein the crystallization-induced dynamic transformation reaction in the step (d) is carried out in the presence of seed and a catalytic amount of base.

13. The process of claim 12, wherein the base is an amine selected from the group consisting of triethylamine, tri(n-butyl)amine, diisopropylethylamine, diisopropylamine, pyridine, 4-dimethylaminopyridine, 4-(4-methyl-piperidine-1-yl)-pyridine, optically active 1-phenylethylamine, and optically active 1-naphthylethylamine.

14. The process of claim 13, wherein the amine is used in an amount of 0.001 to 1.0 equivalent to the compound of formula (14).

15. A pharmaceutical composition comprising the compound of formula (1) according to claim 1 and one or more pharmaceutical pharmaceutically acceptable carriers.

16. The compound of claim 3, wherein the compound is a crystalline form showing the following X-ray diffraction pattern:

| D (X) | Relative strength($I/I_0$) | 2θ Angle |
|---|---|---|
| 9.665 | 0.555 | 9.15 |
| 7.284 | 0.397 | 12.15 |
| 5.825 | 0.260 | 15.21 |
| 5.563 | 0.228 | 15.93 |
| 5.372 | 0.302 | 16.5 |
| 4.840 | 1.000 | 18.33 |
| 4.695 | 0.477 | 18.9 |
| 4.341 | 0.454 | 20.46 |
| 3.663 | 0.230 | 24.3 |
| 3.414 | 0.219 | 26.1. |

17. A compound of the following structure:

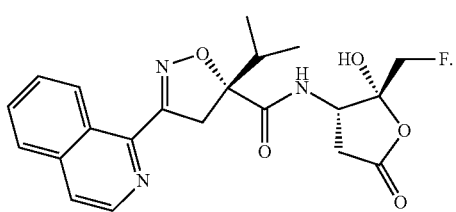

18. A pharmaceutical composition comprising the compound of claim 17 and one or more pharmaceutically acceptable carriers.

19. A process for preparing a compound of claim 17, comprising:
(a) deprotecting the compound of formula (14) to obtain a mixture of the compounds of formula (15) and formula (16); and
(b) treating the mixture of the compounds of formula (15) and formula (16) with a catalytic amount of base together with a seed of the compound of formula (1) to transform both the compound of formula (15) and the compound of formula (16) into the compound of formula (1),
wherein the compound of formula (15) is in equilibrium with the compounds of formula (16), formula (17) and formula (1), and the compound of formula (16) is in equilibrium with the compounds of formula (18) and formula (19),

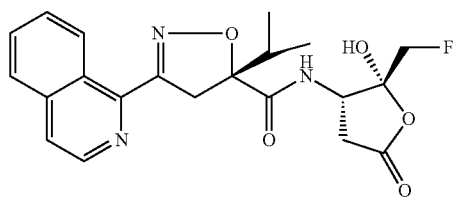

1

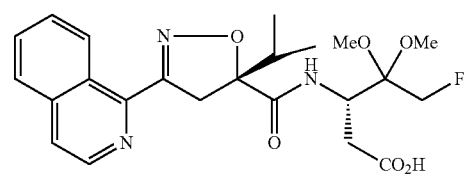

14

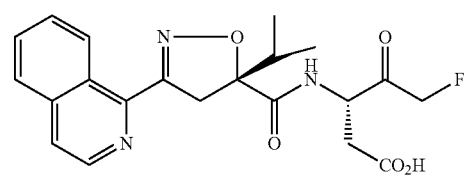

15

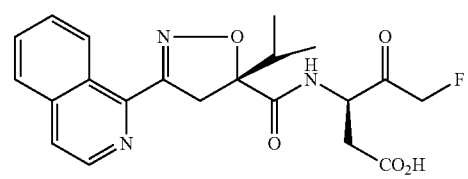

16

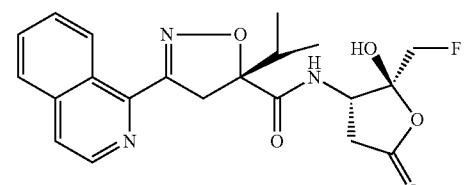

17

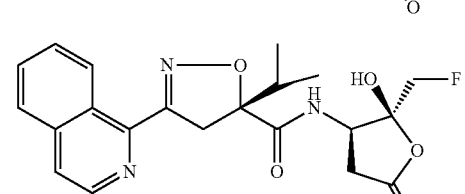

18

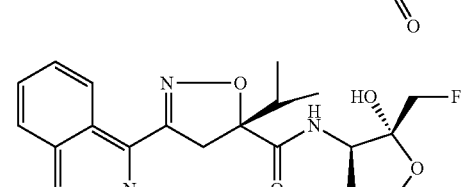

19

* * * * *